(12) United States Patent
Massoni

(10) Patent No.: US 7,758,659 B2
(45) Date of Patent: Jul. 20, 2010

(54) CATALYZED AIR OXIDATION HAIRCOLOR

(75) Inventor: Jack Massoni, New Fairfield, CT (US)

(73) Assignee: Combe Incorporated, White Plains, NY (US)

(*) Notice: Subject to any disclaimer, the term of this patent is extended or adjusted under 35 U.S.C. 154(b) by 0 days.

(21) Appl. No.: 12/310,084

(22) PCT Filed: Jul. 30, 2007

(86) PCT No.: PCT/US2007/016980

§ 371 (c)(1),
(2), (4) Date: Feb. 9, 2009

(87) PCT Pub. No.: WO2008/020983

PCT Pub. Date: Feb. 21, 2008

(65) Prior Publication Data

US 2009/0320215 A1    Dec. 31, 2009

Related U.S. Application Data

(60) Provisional application No. 60/836,876, filed on Aug. 10, 2006.

(51) Int. Cl.
*A61Q 5/10* (2006.01)

(52) U.S. Cl. ............ 8/405; 8/406; 8/408; 8/435; 8/552; 8/611; 8/628

(58) Field of Classification Search ............ 8/405, 8/406, 408, 435, 552, 611, 628
See application file for complete search history.

(56) References Cited

U.S. PATENT DOCUMENTS

| | | | |
|---|---|---|---|
| 4,004,877 A | 1/1977 | Saphir | |
| 4,054,413 A * | 10/1977 | Feinland et al. | 8/410 |
| 4,129,414 A | 12/1978 | Rose | |
| 4,904,274 A | 2/1990 | Schultz | |
| 4,992,077 A | 2/1991 | Tennigkeit | |
| 5,032,138 A | 7/1991 | Wolfram | |
| 5,104,413 A | 4/1992 | Ikeda | |
| 5,167,669 A | 12/1992 | Grollier | |
| 5,173,085 A | 12/1992 | Brown | |
| 5,199,954 A | 4/1993 | Schultz | |
| 5,279,618 A | 1/1994 | Prota | |
| 5,368,610 A | 11/1994 | Chan | |
| 5,637,115 A | 6/1997 | Balzer | |
| 5,735,908 A | 4/1998 | Cotteret | |
| 5,741,337 A | 4/1998 | Bone | |
| 5,795,354 A | 8/1998 | Rippon | |
| 5,873,910 A | 2/1999 | Henrion | |
| 5,961,668 A | 10/1999 | Akram | |
| 6,001,136 A | 12/1999 | Audousset | |
| 6,099,592 A | 8/2000 | Vidal | |
| 6,406,502 B1 | 6/2002 | Audousset | |
| 6,428,580 B2 | 8/2002 | Schultz | |
| 6,485,528 B1 | 11/2002 | Bartels | |
| 6,537,330 B1 | 3/2003 | Hoeffkes | |
| 6,599,328 B1 | 7/2003 | Plos | |
| 6,648,925 B1 | 11/2003 | Mayer | |
| 6,695,888 B2 | 2/2004 | Bartolone | |
| 6,723,136 B2 | 4/2004 | Pruche | |
| 6,733,539 B2 | 5/2004 | Plos | |
| 6,840,964 B1 | 1/2005 | Plos | |
| 6,863,698 B1 | 3/2005 | Hoeffkes | |
| 7,004,980 B2 | 2/2006 | Saito | |
| 2003/0019049 A9 | 1/2003 | Kravtchenko et al. | |
| 2003/0192548 A1 | 10/2003 | Chang | |
| 2004/0255398 A1 | 12/2004 | Saito | |

FOREIGN PATENT DOCUMENTS

| | | |
|---|---|---|
| EP | 0 507 448 A2 | 10/1992 |
| EP | 1 362 578 | 11/2003 |
| WO | WO01/41717 | 6/2001 |
| WO | WO01/97756 A2 | 12/2001 |
| WO | WO02/46165 | 6/2002 |
| WO | WO03/047542 | 6/2003 |
| WO | WO03/074014 | 9/2003 |
| WO | WO03/090700 | 11/2003 |
| WO | WO2005/039510 A2 | 5/2005 |

OTHER PUBLICATIONS

Ochiai et al., J. Cosmetic Soc.,56, 29-46 (2005).
Corbett, Dyes and Pigments, 41, 127-136 (1999).
Motz-Schlack et al.,J. Photochemistry and Photobiology,147, 233-239 (2002).
Tanada et al., Forensic Science Interenational, 64, 1-8 (1994).
Reiss et al., J. Allergy,16, (2) 134-141 (1957).
Motz-Schlack et al.,J. Photochemistry and Photobiology,147, 225-231 (2002).
PCT Search Report dated Jun. 2, 2008.

* cited by examiner

*Primary Examiner*—Eisa B Elhilo
(74) *Attorney, Agent, or Firm*—Hedman & Costigan, P.C.; James V. Costigan

(57) ABSTRACT

An air-oxidation haircolor composition is based: a) water; b) water soluble metal salt as a catalyst; c) etidronic acid (1-hydroxyethane-1,1-diphosphoric acid) as a chelating agent and color deposition enhancer; d) oxidation primary dye intermediates; e) an aromatic triol such as 1,2,4-Benzenetriol; f) auxiliary oxidation dye couplers; g) dye antioxidants and stabilizers; h) optionally, a water soluble surfactant; i) optionally, a water soluble anionic polymer; j) a water soluble solvent system; and k) an alkalizer.

10 Claims, No Drawings

CATALYZED AIR OXIDATION HAIRCOLOR

BACKGROUND OF THE INVENTION

Permanent or oxidation haircoloring products constitute the majority of formulas used in modern times. These have the ability to change the color of gray or pigmented hair, as they permanently alter the hair's coloration. Reapplication occurs as the hair's new growth becomes noticeable. Oxidation hair dyes are normally sold in the form of a two-component kit. In one container is an alkaline composition that contains oxidation dyes and an appropriate vehicle. In the other container is a developer composition that utilizes an oxidizing agent, usually hydrogen peroxide. The two compositions are mixed immediately prior to use and applied to the hair. The alkaline pH of the mixture causes the hair shaft to swell, allowing the dye precursors to penetrate into the cortex of the hair. These dye precursors are then oxidized, which combine to form larger molecules. These larger molecules contain a significant level of resonance, hence producing a colored product that is visible from the exterior of the hair. After an appropriate development time, the mixture is rinsed from the hair. The color of the hair is then permanently altered. Depending upon the pH of the mixture and the strength of the developer, these systems can have the capability to lighten the hair's natural pigment, or only deposit color with little lightening action. The so-called "deposit only permanent colors" have played a minor role in retail women's products marketed in the past 30 years, but have a significant share of the professional market. They also make up the majority of men's hair colorants sold today, due to the natural gray blended appearance that the final results impart.

As the minimal lightening products or "deposit only permanent colors" do not require the natural pigment lightening affect produced with the addition of hydrogen peroxide or similar type of oxidizer, attempts have been made to replace or eliminate the developer portion of the oxidation dye products. In regards to replacing hydrogen peroxide, several inventions discuss the use of enzymes or solutions of chlorites. These systems still require two component compositions that are mixed immediately prior to application. Although the alternate developer formulas are milder and produce less damage to the hair, they do not offer any great advantages in relation to improved convenience, messiness, ease of use, or color delivery. The only products that can make that claim are the so-called air oxidation or auto oxidation hair colors that eliminate the entire mixing step. As the name implies, these compositions rely on atmospheric oxygen for color development. No mixing is required. Formulas are applied to the hair for 15-30 minutes and rinsed. Unfortunately, very little color develops within the hair structure using this process. The first practical application of this technology was first discussed in U.S. Pat. Nos. 3,920,384 and 4,054,413. Traditional primary intermediates were combined with couplers that had a high degree of electron donating groups on the aromatic ring. These couplers are more reactive than most dye intermediates, and were able to produce a small amount of color in the hair structure with limited exposure. Since the amount of color developed was minor, the only commercial application for such formulas was in the gradual or progressive hair color field. Consequently, a few products were eventually marketed to men in an attempt to find a safer means of gradually coloring hair. Prior to these products, lead acetate compositions were the only means of accomplishing this. Both types of products require reapplication of the formulas several times a week in order to develop and maintain any degree of gray coverage. To this day these air oxidation gradual haircolors only play a minor role, even in the men's haircoloring arena.

Catalyzed dying systems have been explored in the past for two component oxidation haircolor systems, in an effort to speed up the processing time or produce darker shades on very resistant hair. These rely on some type of pretreatment containing the catalyst (usually a water soluble transition metal salt). The extra pre-treatment step usually made these products impractical for commercial application. Additionally, the build up of copper or iron within the protein matrix left the hair feeling rough and damaged. Attempts to apply the metal catalyst technology to air oxidation color development have been made with limited success. U.S. Pat. No. 4,004,877 uses metal salts complexed with tartaric acid in an air oxidation system. The resulting colors on hair are still very light with a single application. Additionally, the composition requires the use of formamide as solvent. For safety reasons, this material is no longer acceptable for use in cosmetic products. U.S. Pat. No. 6,648,925 takes this technology a step further by capturing the metal catalyst within a clathrate or zeolite compound in an air oxidation composition. These are inclusion complexes where the metal ions are completely enclosed within the crystal structure of another compound. These are difficult formulations to prepare, and are not practical for commercial application. Also, these formulas do not develop enough color on gray hair to produce an entire palette for a typical population. U.S. Pat. No. 7,060,108 teaches the use of iron salts chelated with EDTA compounds in order to enhance dye take with minimal damage. Even under the more extreme dying conditions cited in this patent (30 minutes dwell at 30° C.); formulations tested on hair swatches also do not produce shades comparable to two part "deposit only oxidation haircolor".

The object of this invention is to provide formulations and manufacturing methods that achieve the level of color deposition, and wear properties equivalent to two part "deposit only oxidation haircolorants", but from a single component air oxidation product. These formulations use known dye intermediates and other cosmetic ingredients in unique combinations which produce an unexpected degree of gray coverage. Additionally, due to the absence of an oxidizing agent other than atmospheric oxygen, the compositions are milder, less damaging to the hair, and have better color retention than traditional two part systems.

SUMMARY OF INVENTION

The invention includes a specific catalyzed air oxidation haircolor composition that will provide a significant increase in gray coverage over existing technology, while maintaining safety, good wear properties, and ease of use. The consistency of the formulas may be modified to produce a gel or slightly viscous lotion suitable for dispensing from an aerosol container. The compositions provided by this invention are susceptible to premature air oxidation, and must therefore be prepared and stored under anaerobic conditions. The composition should contain the following ingredients:

1. 70-95% water 2. 0.1-1.0% of a water soluble metal salt 3. 0.03-0.3% of etidronic acid 4. 0.1-5% of oxidation dyes considered a primary intermediates 5. 0.1-3% of an aromatic triol 6. 0-3% or preferably 0.1-3% of auxiliary oxidation dyes 7. 0.1-0.3% antioxidants and stabilizers 8. 1-5% of a water soluble surfactant that is anionic, amphoteric, nonionic, or a combination of such surfactants 9. 0.5-2.0% of a water soluble anionic polymer such as a carbomers 10. 0.5-10% of an organic solvent system such as one consisting of a combination of isopropanol and isopropyl acetate, or ethanol and ethyl acetate.

11. A quantity sufficient of a cosmetically acceptable alkalizer to achieve a final pH of 9.0-10.0.

DETAILED DESCRIPTION OF THE INVENTION

The vehicle used to carry the dye intermediates allows for very high levels of water in the finished formulas. In this invention the water can range from 70-95% of the composition. Lighter shades using fewer dyes will be at the higher end of the range, while dark brown and black shades will be closer to the 70% level. This high level of water creates a very efficient carrier for the dye systems, which normally would not deposit on gray hair to the level that is present for the formulas covered by this invention.

In order to achieve maximum gray coverage potential of the air oxidation haircolor compositions covered in this invention, the formulas need to catalyze the oxidation process within the hair structure. The preferred catalysts are water soluble metal salts include copper, cobalt, zinc, silver, nickel and iron salts, preferably with non-toxic anions such as the sulfate, chloride, nitrate, carbonate, phosphate or organic acid salts such as the fumarate, citrate, tartrate and the like. Water soluble manganese salts are preferred because they create the most color deposition when added to the formulas at levels of 0.1-1.0%. More preferably, the concentration of the anhydrous salt should 0.3-0.7%, based on the total weight of the salt in the composition. Dye take on gray hair will drop off on either side of the above mentioned ranges. The most preferred anions to be used in conjunction with manganese are sulfate or chloride, although nitrates, carbonates, phosphates, fluoride, or bromide are acceptable.

Additional color enhancement on gray hair can be achieved by the addition of a specific chelating agent called etidronic acid or also known as 1-hydroxyethane-1,1-diphosphonic acid. The structure is indicated below.

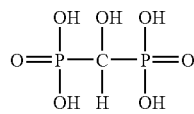

In addition to the added color take with the use of etidronic acid, the chelating affect with the manganese ions, helps limit the amount of manganese that remains within the hair structure after the compositions are removed by rinsing and shampooing. Some metal ions such as copper or iron, will leave the hair feeling rough and damaged. Manganese's affect on hair is not as dramatic as the more common transition metals, but it is still prudent to limit the amount remaining in the hair after a color treatment. The amount of etidronic acid required works well from 0.03-0.3% when used with the prescribed level of manganese salt. Below this range the color saturation drops off, and above the 0.3% level long term stability is compromised and color delivery is also negatively impacted.

The air oxidation colorants discussed in this invention use conventional oxidation dye primary intermediates. The most useful of these include: p-Phenylenediamine, N,N-Bis(2-Hydroxyethyl)-p-Phenylenediamine Sulfate, p-Aminophenol, and p-Toluenediamine. Others can include: 2-Chloro-p-Phenylenediamine, N-Phenyl-p-Phenylenediamine, p-Methylaminophenol, 1-Amino-4-(2-Methoxyethyl)-aminobenzene, 2,4,5,6-Tetraminopyrimidine, 2-(Hydroxymethyl)-p-Phenylenediamine, 3-Methyl-p-Aminophenol, 2-(2-Hydroxyethyl)-p-Phenylenediamine, 4,4'-Diaminodiphenylamine, 1,3-Dimethyl-2,5-Diaminobenzene, 2-isopropyl-p-Phenylenediamine, N-(beta-hydroxypropyl)-p-Phenylenediamine, 2-Methyl-p-Aminophenol, 2-Propyl-p-Phenylenediamine, 2-(2'-Hydroxyethylaminomethyl)-p-Aminophenol, 2-(Methoxymethyl)-p-Aminophenol, 2-Methyl-4-Dimethylaminoaniline, 5-Aminosalicylic Acid, and other related compounds. Depending upon depth of shade for the resulting composition, the level of use should vary from 0.1% in the lightest blonde shades to 5% in the darkest shades.

The invention includes the use of aromatic triols such as 1,2,4-benzenetriol, 1,3,5-triethylhydroxybenzene, tris(2-hydroxyethyl)isocyanurate and the like as the useful dye couplers in all compositions. The preferred coupler is 1,2,4-benzenetriol. This material will combine with the primary intermediates in the preceding paragraph to form the oxidation condensate which is trapped within the hair structure. These compounds produce the majority of the brown coloration for the formulas derived from this technology. The dye concentration should vary from 0.1% to 3% depending upon the final depth of color desired. This material is very oxygen sensitive in the dry form, therefore all 1,2,4-Benzenetriol used in the compositions outlined by this technology is formed in solution by acid hydrolysis of the triacetoxy version of this compound. The hydrolysis is carried out in ethanol or isopropanol by heating with a small amount of sulfuric acid to 50° C. for up to 6 hours. The resulting solution will yield 10-20% of 1,2,4-Benzenetriol or other aromatic triol depending upon the exact formulation of the starting materials.

The formulas may be modified by the addition of other dye couplers. The most useful of these include: Resorcinol, 4-Chlororesorcinol, 2-Methylresorcinol, m-Aminophenol, 1-Naphthol, 1,5-Naphthalenediol, 2,7-Napthalenediol, 2,4-Diaminophenol, Hydroxybenzomorpholine, 1-Hydroxy-3-Dimethylaminobenzene, 4-Amino-2-Hydroxytoluene, 2-Methyl-5-Hydroxyethylaminophenol, 1-Methoxy-2,5-Diaminobenzene, Phenyl Methyl Pyrazolone, 2,4-Diaminophenoxyethanol HCl, 4-Ethoxy-m-Phenylenediamine, 1-Hydroxy-3-amino-4,6-Dichlorobenzene, 1-Hydroxy-2,5-Diamino-4-methoxybenzene, 4-Amino-m-Cresol, 6-Amino-m-Cresol, 2-amino-4-Hydroxyethylaminoanisole, 5-Amino-6-Chloro-o-Cresol, 6-Amino-o-Cresol, 4,6-Bis(2-Hydroxyethoxy)-m-Phenylenediamine HCl, 5-Amino-4-Chloro-o-Cresol, and other related compounds. Depending upon the depth of shade for the resulting composition, the level of use should vary from 0.1-3%.

A small amount of antioxidants or reducing agents should be used to maximize the shelf life of the finished product. A typical two part oxidation haircolor system will use up to 1% of antioxidants to ensure stability during manufacture and in the final package. This level is too high in order to achieve the highest level of color deposition on the hair. When antioxidants are used singularly or in combination in this composition, the range to be used in this invention should be 0.1-0.3% of the total formula. Below this level will result in poor long term stability, and above the designated range will result in poor color deposition. The most appropriate reducing agents may include: sodium sulfite, bisulfite salts, thioglycolate salts, erthorbic acid, ascorbic acid, thiosulfate salts, and other related materials.

Low levels of surfactants are required in the formulas in order to quickly wet out the hair, produce lather, and allow for ease of rinsing. The concentration should be restricted to 1-5% of the total formula. By keeping to this range, the products maintain their high water content and the resulting efficiency in delivering color to the hair. These surfactants can be any cosmetically acceptable anionic, amphoteric, or non-ionic material that will produce sufficient lather. These can be as simple as Alkyl sulfates, Alkyl ether sulfates, or fatty acid soaps. More preferably the surfactants should produce a milder affect on the skin, as the working pH of the formulas is between 9 and 10. These can include: Amphoacetates, Alkyl polyglycosides, Amphodiacetaes, Amphohydroxypropylsulfonates, Amphopropionates, Amidopropyl Betaines, Sultaines, Alkylamidopropylamine Oxides, Alkylamine Oxides, Alkanolamides, Sulfocuccinates, and related compounds.

To achieve an adequate viscosity and ideal rheological properties to allow for ease of product application and adherence to the hair, the formulas should be thickened with water soluble anionic polymers referred to as Carbomer. These provide the necessary parameters mentioned above, allow for high water content of the formulas, and stability with the dye intermediates and manganese salt. The most common of these are called carbomers, which are manufactured by the Noveon Corporation under the Carbopol name. These can be described as high molecular weight homo and copolymers of acrylic acid cross linked with a polyalkenyl polyether having a viscosity, as measured in water, at 0.5-1.0% w/v of about 3,000-60,000 mPa s. Examples of these include: Carbopol Ultrez 10, Carbopol 940, Carbopol 941, Carbopol 980, Carbopol ETD 2050, Carbopol 981, Carbopol 934, Carbopol 2984, and Carbopol 5984. Similar materials are produced by other manufacturers and can go by the CTFA designation of carbomer. These materials should be used in the formulations at 0.5-2.0% to produce a moderately viscous liquid to a gel form.

A water soluble solvent system is used to assist in dye solubility and help in carrying the dye intermediates to the hair's cortex. These solvents are contained within the aromatic triol or in particular, the benzentriol premix, and are a result of the reaction from benzenetriacetate to the triol form. Either isopropanol or ethanol can be used as a medium to carry out this reaction. The resulting solution will contain the aromatic triol such as the 1,2,4-Trihydroxybenzene, plus the alcohol, plus the corresponding acetate compound (either ethyl acetate or isopropyl acetate) depending on the particular aromatic triol. The final formulation will contain 0.5-10% of these solvent systems depending upon the level of the aromatic triol such as benzenetriol that is a required for the particular shade.

The best color deposition for the formulas contained within this invention occurs from pH 9-10. A quantity sufficient of a cosmetically acceptable alkalizer to achieve this pH is required. The alkalizer can either be organic or inorganic in nature. These can include ethanolamine, triethanolamine, aminomethyl propanol, ammonium hydroxide, carbonates, bicarbonates, and other similar materials.

Experimental Procedures and Results:

The following is a list of various shades that can be produced by using the technology discussed in this invention. The shade descriptor is matched on 90% bended gray hair as dyed out in the laboratory, and on clients as listed in Table II. In all instances the development time was 10 minutes, followed by rinsing, shampooing, and blow drying.

TABLE I

Catalyzed Air Oxidation Formulas

| Ingredients | Ex. 1 Dark Blonde Wt % | Ex. 2 Light Brown Wt % | Ex. 3 Medium Brown Wt % | Ex. 4 Dark Brown Wt % | Ex. 5 Black Wt % |
|---|---|---|---|---|---|
| D.I. Water | 92.745 | 89.000 | 84.470 | 77.250 | 72.000 |
| Manganese Sulfate | 0.200 | 0.400 | 0.500 | 0.600 | 0.700 |
| Etidronic Acid | 0.100 | 0.050 | 0.030 | 0.200 | 0.300 |
| Erythorbic Acid | 0.050 | 0.100 | 0.150 | 0.150 | 0.200 |
| Sodium Sulfite | 0.050 | 0.050 | 0.100 | 0.100 | 0.100 |
| Decyl Glucoside | — | — | 3.000 | — | — |
| Disodium Lauryl-Amphodiacetate | 2.000 | — | — | — | — |
| Cocoamidopropyl Betaine | — | 3.000 | — | — | — |
| Oleamine Oxide | — | — | — | 2.500 | — |
| Sodium Laureth Sulfate | — | — | — | — | 2.000 |
| Ultrez 10 (Carbomer) | 1.000 | — | 1.100 | — | 1.300 |
| Carbopol 941 | — | 1.100 | — | 1.300 | — |
| Aminomethyl Propanol | 2.000 | — | 4.250 | — | 6.500 |
| Triethanolamine | — | 3.000 | — | — | — |
| Monoethanolamine | — | — | — | 5.000 | — |
| 1,2,4-Benzenetriol | 0.300 | 0.500 | 0.900 | 2.000 | 2.500 |
| Isopropyl Alcohol | 0.500 | — | 1.600 | — | 4.500 |
| Isopropyl Acetate | 0.350 | — | 1.100 | — | 3.000 |
| Ethanol | — | 0.900 | — | 3.600 | — |
| Ethyl Acetate | — | 0.600 | — | 2.400 | — |
| p-Phenylenediamine | 0.280 | 0.500 | 0.950 | 1.500 | 3.000 |
| p-Toluenediamine | — | — | — | — | 1.000 |
| p-Aminophenol | 0.180 | 0.350 | 0.350 | 0.200 | — |
| N,N-Bis(2-Hydroxyethyl)-p-Phenylenediamine Sulfate | 0.015 | 0.250 | 0.800 | 1.500 | — |
| m-Aminophenol | 0.030 | 0.100 | 0.500 | 1.000 | 2.000 |
| 2-Methyl-5-Hydroxyethylamino-phenol | 0.200 | 0.100 | 0.200 | 0.100 | — |
| 2,4-Diaminophenoxy ethanol sulfate | — | — | — | 0.300 | 0.300 |
| 2-Amino-4-Hydroxyethylamino-anisole sulfate | — | — | — | 0.300 | 0.600 |

The dyeouts from examples 1 through 5 and throughout this document were measured using a Minolta 508d spectrophotometer using the Hunter L,a,b scale. It is typical in the industry to use this scale to measure color. In general, measurements are reproducible and visually noticeable at + or −"0.5" for any parameter.

| Color Measurement | | | |
|---|---|---|---|
| Sample | "L" | "a" | "b" |
| Untreated 90% blended gray hair | 57.1 | −0.6 | 9.4 |
| Example 1 | 34.3 | 2.3 | 6.7 |
| Example 2 | 27.9 | 2.8 | 6.5 |
| Example 3 | 25.2 | 2.1 | 4.9 |
| Example 4 | 20.5 | 1.3 | 4.5 |
| Example 5 | 15.8 | 0.8 | 1.0 |

"L" = lightness, + is lighter and − is darker
"a" = relative amounts of red and green, + is more red and − is greener
"b" = relative amounts of yellow and blue, + is more yellow and − is bluer The same formulas indicated in examples 1 through 5 were tested on salon clients for a six month period. Re-applications were made every 5 weeks. Upon return, no unusual wash out was noted. All shades wore on tone, and were within one level of the original color that was applied previously. The colors produced for all formulas were indicative for a typical deposit-only haircolor with the same shade descriptor.

TABLE II

Catalyzed air oxidation client study (January-July 2006)

| Client | Shade | Applications | Results |
|---|---|---|---|
| 1 | Dark Blonde | 2 | Level 7, good coverage, cool tone |
| 2 | Dark Blonde | 5 | Level 7.5, good coverage, blue/violet |
| 3 | Dark Blonde | 3 | Level 8, good coverage, neutral tone |
| 4 | Dark Blonde | 3 | Level 8.5, light coverage, cool tone |
| 5 | Dark Blonde | 3 | Level 7, good coverage, neutral tone |
| 6 | Light Brown | 2 | Level 6, good coverage, cool neutral |
| 7 | Light Brown | 5 | Level 6, good coverage, BV tone |
| 8 | Light Brown | 5 | Level 6, good coverage, BV tone |
| 9 | Light Brown | 4 | Level 6.5, good coverage, cool tone |
| 10 | Light Brown | 5 | Level 5.5, good coverage, cool tone |
| 11 | Light Brown | 3 | Level 6, good coverage, BV tone |
| 12 | Light Brown | 5 | Level 6.5, good coverage, cool tone |
| 13 | Light Brown | 1 | Level 5, good coverage, neutral tone |
| 14 | Light Brown | 5 | Level 6.5, good coverage, BV tone |
| 15 | Light Brown | 4 | Level 6.5, good coverage, BV tone |
| 16 | Light Brown | 3 | Level 6, good coverage, cool tone |
| 17 | Light Brown | 3 | Level 6.5, good coverage, neutral tone |
| 18 | Light Brown | 3 | Level 6, good coverage, neutral tone |
| 19 | Medium Brown | 5 | Level 5.5, average coverage, BV tone |
| 20 | Medium Brown | 4 | Level 5, good coverage, BV tone |
| 21 | Medium Brown | 6 | Level 5.5, good coverage, cool tone |
| 22 | Medium Brown | 3 | Level 5.5, Excellent coverage, neutral |
| 23 | Medium Brown | 5 | Level 5.5, good coverage, BV tone |
| 24 | Medium Brown | 4 | Level 5, good coverage, BV tone |
| 25 | Medium Brown | 2 | Level 4.5, good coverage, neutral tone |
| 26 | Medium Brown | 5 | Level 5, good coverage, BV tone |
| 27 | Medium Brown | 1 | Level 5, good coverage, BV tone |
| 28 | Medium Brown | 6 | Level 5, good coverage, BV tone |
| 29 | Medium Brown | 6 | Level 5.5, good coverage, neutral tone |
| 30 | Medium Brown | 2 | Level 5, good coverage, neutral tone |
| 31 | Dark Brown | 1 | Level 4, good coverage, neutral tone |
| 32 | Dark Brown | 3 | Level 4, good coverage, neutral tone |
| 33 | Dark Brown | 2 | Level 2, good coverage, cool tone |
| 34 | Dark Brown | 4 | Level 3.5, good coverage, cool tone |
| 35 | Dark Brown | 5 | Level 3.5, good coverage, cool tone |
| 36 | Black | 5 | Level 1, good coverage, BV tone |
| 37 | Black | 3 | Level 1, good coverage, BV tone |
| 38 | Black | 1 | Level 2, good coverage, BV tone |
| 39 | Black | 2 | Level 1, good coverage, BV tone |

Level 10 = Extra Light Blonde
Level 9 = Light Blonde
Level 8 = Medium Blonde
Level 7 = Dark Blonde
Level 6 = Light Brown
Level 5 = Medium Brown
Level 4 = Medium/Dark Brown
Level 3 = Dark Brown
Level 2 = Dark Brown/Black
Level 1 = Black
BV = blue violet The Medium Brown shade in example 3 was used as the control for the remainder of the experiments, while other parameters were varied to confirm the optimum ranges provided in the claims for this invention.

TABLE 3

| | Sample | | | | |
|---|---|---|---|---|---|
| | Ex. 6 Wt % | Ex. 7 Wt % | Ex. 8 Wt % | Ex. 9 Wt % | Ex. 10 Wt % |
| Water | 67.470 | 86.220 | 85.220 | 81.720 | 84.920 |
| Manganese Sulfate | 0.500 | 0.500 | 0.500 | 0.500 | 0.050 |
| Etidronic Acid | 0.030 | 0.030 | 0.030 | 0.030 | 0.030 |
| Erythorbic Acid | 0.150 | 0.150 | 0.150 | 0.150 | 0.150 |
| Sodium Sulfite | 0.100 | 0.100 | 0.100 | 0.100 | 0.100 |
| Decyl Glucoside | 10.000 | 3.000 | 3.000 | 3.000 | 3.000 |
| Ultrez 10 (Carbomer) | 1.100 | 1.100 | 1.100 | 1.100 | 1.100 |
| Sodium Lauryl Sulfate | 10.000 | — | — | — | — |
| Aminomethyl Propanol | 4.250 | 2.500 | 3.500 | 7.000 | 4.250 |
| 1,2,4-Benzenetriol | 0.900 | 0.900 | 0.900 | 0.900 | 0.900 |
| Isopropyl Alcohol | 1.600 | 1.600 | 1.600 | 1.600 | 1.600 |
| Isopropyl Acetate | 1.100 | 1.100 | 1.100 | 1.100 | 1.100 |
| p-Phenylenediamine | 0.950 | 0.950 | 0.950 | 0.950 | 0.950 |
| p-Aminophenol | 0.350 | 0.350 | 0.350 | 0.350 | 0.350 |
| N,N-Bis(2-Hydroxyethyl)-p-Phenylenediamine Sulfate | 0.800 | 0.800 | 0.800 | 0.800 | 0.800 |
| m-Aminophenol | 0.500 | 0.500 | 0.500 | 0.500 | 0.500 |
| 2-Methyl-5-Hydroxyethyl-aminophenol | 0.200 | 0.200 | 0.200 | 0.200 | 0.200 |
| | | pH = 6.9 | pH = 8.8 | pH = 10.3 | |

The water content of the formulas for these air oxidation colorants has a significant impact on the amount of color deposition within hair and other keratin fibers. A minimum water content of 70% is required in order to maximize the color take. Even with formulas that have slightly less water, as with example 6, the depth of color on gray hair begins to drop off. Example 6 was dyed out for 10 minutes on 90% gray hair and compared to the control Medium Brown shade used in example 3. The swatch appearance for example 6 was more like a shade in between dark blonde and light brown. L.a.b readings confirm this observation.

| Dyeouts on 90% Gray Hair for 10 minutes | | | |
|---|---|---|---|
| Sample | "L" | "a" | "b" |
| Example 3 (control Medium Brown shade) | 25.2 | 2.1 | 4.9 |
| Example 6 (lower water content) | 30.1 | 2.2 | 5.2 |

The pH of the compositions requires a restriction of pH 9 to pH 10. Formulations on either side of this range show lighter color deposition than the control Medium Brown shade of example 3. This formula has a pH of 9.3. Examples 7, 8, and 9 were prepared at pH 6.9, 8.8, and 10.3; respectively. Even the products that are close to the desired range show some indication of lighter color deposition than the control. All formulas were dyed out for 10 minutes on 90% gray hair and compared to the control Medium Brown shade used in example 3. L.a.b. readings are illustrated in the chart below.

| Dyeouts on 90% Gray Hair for 10 minutes | | | |
|---|---|---|---|
| Sample | "L" | "a" | "b" |
| Example 3 (Control Medium Brown shade, pH 9.3) | 25.2 | 2.1 | 4.9 |

-continued

| Dyeouts on 90% Gray Hair for 10 minutes | | | |
|---|---|---|---|
| Sample | "L" | "a" | "b" |
| Example 7 (pH 6.9) | 36.7 | 0.4 | 9.3 |
| Example 8 (pH 8.8) | 27.1 | 1.7 | 5.3 |
| Example 9 (pH 10.3) | 35.9 | 2.6 | 6.3 |

TABLE 4

| | Sample | | | | |
|---|---|---|---|---|---|
| | Ex. 11 Wt % | Ex. 12 Wt % | Ex. 13 Wt % | Ex. 14 Wt % | Ex. 15 Wt % |
| Water | 84.970 | 82.970 | 84.200 | 84.500 | 88.070 |
| Manganese Sulfate | — | 2.000 | 0.500 | 0.500 | 0.500 |
| Etidronic Acid | 0.030 | 0.030 | 0.300 | — | 0.030 |
| Erythorbic Acid | 0.150 | 0.150 | 0.150 | 0.150 | 0.150 |
| Sodium Sulfite | 0.100 | 0.100 | 0.100 | 0.100 | 0.100 |
| Decyl Glucoside | 3.000 | 3.000 | 3.000 | 3.000 | 3.000 |
| Ultrez 10 (Carbomer) | 1.100 | 1.100 | 1.100 | 1.100 | 1.100 |
| Aminomethyl Propanol | 4.250 | 4.250 | 4.250 | 4.250 | 4.250 |
| 1,2,4-Benzenetriol | 0.900 | 0.900 | 0.900 | 0.900 | — |
| Isopropyl Alcohol | 1.600 | 1.600 | 1.600 | 1.600 | — |
| Isopropyl Acetate | 1.100 | 1.100 | 1.100 | 1.100 | — |
| p-Phenylenediamine | 0.950 | 0.950 | 0.950 | 0.950 | 0.950 |
| p-Aminophenol | 0.350 | 0.350 | 0.350 | 0.350 | 0.350 |
| N,N-Bis(2-Hydroxyethyl)-p-Phenylenediamine Sulfate | 0.800 | 0.800 | 0.800 | 0.800 | 0.800 |
| m-Aminophenol | 0.500 | 0.500 | 0.500 | 0.500 | 0.500 |
| 2-Methyl-5-Hydroxyethyl-aminophenol | 0.200 | 0.200 | 0.200 | 0.200 | 0.200 |

The manganese salt concentration performs best in regards to color delivery on hair when used at a level of 0.1-1.0%. The control formula of the Medium Brown shade shown in example 3 contains 0.5% manganese sulfate. Examples 10, 11 and 12 uses 0.05%, 0% and 2% manganese sulfate respectively. These compositions that are just outside the range of the invention indicate lower color deposition as illustrated by the dyeouts and color measurements taken in the chart below. All formulas were dyed out for 10 minutes on 90% gray hair and compared to the control Medium Brown shade used in example 3. L.a.b. readings were taken for each swatch.

| Dyeouts on 90% Gray Hair for 10 minutes | | | |
|---|---|---|---|
| Sample | "L" | "a" | "b" |
| Example 3 (Control Medium Brown shade, 0.5% manganese sulfate) | 25.2 | 2.1 | 4.9 |
| Example 10 (0.05% manganese sulfate) | 32.1 | 2.4 | 6.6 |
| Example 11 (no manganese sulfate) | 35.5 | 2.3 | 6.4 |
| Example 12 (2.0% manganese sulfate) | 29.1 | 1.4 | 5.2 |

The Etidronic Acid used within the context of this invention works best at concentrations of 0.03-0.300. At the upper limits, the color deposition on hair is starting to diminish but is still useful. The control Medium Brown shade uses 0.03% etidronic acid. Examples 13 and 14 use 0.3% and 0% etidronic acid respectively. All formulas were dyed out for 10 minutes on 90% gray hair and compared to the control Medium Brown shade used in example 3. L.a.b readings are illustrated in the chart below.

| Dyeouts on 90% Gray Hair for 10 minutes | | | |
|---|---|---|---|
| Sample | "L" | "a" | "b" |
| Example 3 (Control Medium Brown shade, 0.03% etidronic acid) | 25.2 | 2.1 | 4.9 |
| Example 13 (0.3% etidronic acid) | 26.3 | 2.2 | 5.3 |
| Example 14 (no etidronic acid) | 29.3 | 2.4 | 6.1 |

There are many examples of publications and patents that do not use benzenetriol or similar dye couplers in air oxidation formulas. However, the degree of color take and gray coverage on hair is severely impacted by the absence of these materials. The control Medium Brown shade in example 3 was made up without the 1,2,4-Benzenetriol. The corresponding solvent package that is used in preparation of the triol dye is not required and was also removed from the formula. Example 15 illustrates this change. Using example 3 as a control, the formulas were dyed out for 10 minutes on 90% gray hair. L.a.b. readings are shown in the chart below.

| Dyeouts on 90% Gray Hair for 10 minutes | | | |
|---|---|---|---|
| Sample | "L" | "a" | "b" |
| Example 3 (Control Medium Brown shade, 0.9% 1,2,4-Benzenetriol) | 25.2 | 2.1 | 4.9 |
| Example 15 (no 1,2,4-Benzenetriol) | 42.8 | −0.6 | 7.5 |

A typical formula to convert benzenetriacetate to benzenetriol would be shown in example 16. However, the amounts can vary significantly, and is only limited by the solubility of the triol. Example 16 would yield a solution of about 10% benzenetriol.

Example 16

| Ingredient | WT % |
|---|---|
| D.I. Water | 25.000 |
| Isopropanol | 50.000 |
| Sulfuric acid | 5.000 |
| 1,2,4-Triacetoxybenzene | 20.000 |

Procedure for Preparation of Benzenetriol Solution:
1) Add of the ingredients into a stainless steel mixing container with agitation in the following order: water, isopropanol, 1,2,4-Triacetoxybenzene, and sulfuric acid.
2) Heat with a reflux apparatus attached to the top of the vessel to 50° C. for 4 to 6 hours.
3) Completion of the reaction is signaled by solubility of all dye particles.
4) Cool the batch to room temp and store in a sealed container.

Procedure for the Preparation of Dye Compositions:
1) To a jacketed stainless steel batch vessel fitted with a counter rotating crème mixer or propeller mixer, add 90% of the water, and disperse the Ultrez 10 with agitation. Heat the batch to 60-65° C.
2) Dissolve the antioxidants, etidronic acid, and dyes with mixing.
3) Prepare a premix using 10% of the water and manganese sulfate. Heat the batch to 50° C.

4) Add the surfactants to the batch.

5) Cool the batch to 40-45° C., and add the benzenetriol premix.

6) Add the alkalizer and fragrance to the batch with mixing.

7) Add the manganese sulfate premix to the batch. Mix until uniform. Fill in tubes and seal immediately.

Note: All batching and filling of product should be undertaking at low oxygen levels.

The composition is applied to hair without mixing with an oxidizing agent, and left on the hair for 5-15 minutes, rinsed and shampooed.

In the specification and the claims, all percents are by weight based on the total weight of all components of the composition. As used herein, "moderately viscous" means a viscosity of 500-5000 cps as determined by a Brookfield Viscometer, model number DV-E, using spindle T-C at 6 rpm at a temperature of 23° C.

The invention claimed is:

1. A single component air oxidation hair color composition comprising:
    a) water;
    b) a catalyst of water soluble metal salt selected from the group consisting of manganese sulfate and manganese chloride and wherein the metal salt content is 0.1 to 1.0%;
    c) etidronic acid (1-hydroxyethane-1,1-diphosphonic acid) as a chelating agent and color deposition enhancer;
    d) oxidation primary dye intermediates;
    e) a compound 1,2,4-Benzenetriol;
    f) auxiliary oxidation dye couplers;
    g) dye antioxidants and stabilizers;
    h) optionally, a water soluble surfactant;
    i) optionally, a water soluble anionic polymer;
    j) a water soluble solvent system selected from the group consisting of isopropanol and isopropyl acetate, or ethanol and ethyl acetate, wherein the total solvent system content is 0.5 to 10% of the total composition; and
    k) an alkalizer.

2. An air oxidation hair color composition as defined in claim 1 where the water content is 70-95% by formula weight.

3. An air oxidation hair color composition as defined in claim 1 where the etidronic acid content is 0.03-0.30%.

4. An air oxidation hair color composition as defined in claim 1 where the oxidation primary dye intermediates content is 0.1-5%.

5. An air oxidation hair color composition as defined in claim 1 where compound 1,2,4-Benzenetriol content is 0.1-3.0%.

6. An air oxidation hair color composition as defined in claim 1 where the auxiliary oxidation dye coupler content is 0.1-3.0%.

7. An air oxidation hair color composition as defined in claim 1 where the dye antioxidant and stabilizer content is 0.1-0.3%.

8. An air oxidation hair color composition as defined in claim 1 where the water soluble surfactants consist of a cosmetically acceptable anionic, amphoteric, or nonionic surfactant where the content is 1-5%.

9. An air oxidation hair color composition as defined in claim 1 where the water soluble anionic polymer content is sufficient to produce a moderately viscous liquid to a gel, at concentrations of 0.5% to 2% total solids.

10. An air oxidation hair color composition as defined in claim 1 where an alkalizer is selected from the group consisting of aminomethyl propanol, triethanolamine, monoethanolamine, ammonia, carbonates, bicarbonates, or other cosmetically acceptable materials, used at a concentration sufficient to the bring the pH range of the composition to 9.0-10.0.

* * * * *